United States Patent
Chen

(10) Patent No.: US 9,216,135 B2
(45) Date of Patent: Dec. 22, 2015

(54) MASSAGE APPLIANCE CAPABLE OF SYNCHRONOUS KNEADING AND TAPPING

(71) Applicant: Jue-Yao Chen, Erlin Township, Changhua County (TW)

(72) Inventor: Jue-Yao Chen, Erlin Township, Changhua County (TW)

(73) Assignee: Listore International Co., Ltd., Changhua County (TW)

( * ) Notice: Subject to any disclaimer, the term of this patent is extended or adjusted under 35 U.S.C. 154(b) by 513 days.

(21) Appl. No.: 13/756,575

(22) Filed: Feb. 1, 2013

(65) Prior Publication Data
US 2014/0221886 A1 Aug. 7, 2014

(51) Int. Cl.
| A61H 1/00 | (2006.01) |
| A61H 23/00 | (2006.01) |
| A61H 7/00 | (2006.01) |
| A61N 5/06 | (2006.01) |

(52) U.S. Cl.
CPC .............. *A61H 23/006* (2013.01); *A61H 7/007* (2013.01); *A61N 5/0625* (2013.01); *A61H 2201/0149* (2013.01); *A61H 2201/0207* (2013.01); *A61H 2201/10* (2013.01); *A61H 2201/1215* (2013.01); *A61H 2201/149* (2013.01); *A61H 2201/1623* (2013.01); *A61H 2201/1669* (2013.01); *A61H 2201/1678* (2013.01); *A61H 2205/081* (2013.01); *A61N 2005/0659* (2013.01)

(58) Field of Classification Search
CPC ............ A61H 1/00; A61H 1/006; A61H 7/00; A61H 7/007; A61H 23/00; A61H 23/006; A61H 2201/0149; A61H 2201/0207; A61H 2201/10; A61H 2201/1215; A61H 2201/1623; A61H 2201/1654; A61H 2201/1678; A61H 2201/149; A61H 2201/1669; A61H 2201/1427; A61H 2205/04; A61H 2205/081; A61H 2205/062; A61H 2205/0659
See application file for complete search history.

(56) References Cited

U.S. PATENT DOCUMENTS

| 2004/0186398 | A1* | 9/2004 | Furuie | A61H 15/0078 601/99 |
| 2008/0009777 | A1* | 1/2008 | Chiu | A61H 15/00 601/99 |
| 2011/0275968 | A1* | 11/2011 | Liu | A61H 7/007 601/134 |
| 2012/0232445 | A1* | 9/2012 | Lev | A61H 23/0254 601/112 |

* cited by examiner

*Primary Examiner* — Quang D Thanh
(74) *Attorney, Agent, or Firm* — Alan D. Kamrath; Kamrath IP Lawfirm, P.A.

(57) ABSTRACT

A massage appliance capable of synchronous kneading and tapping includes: a power-driven vertically-moving device, including an outer portion having therein a sliding channel, and a vertically-moving rack disposed alongside the sliding channel; a device capable of synchronous kneading and tapping, including a housing portion having therein a power source for driving a first transmission device whereby a second transmission device is driven to drive a rotational inclined surface structure for driving an oscillating arm to oscillate laterally; an oscillating arm coupled to a massage head support, two infrared lamp plates and two massage heads, causing the massage heads to perform kneading-based massage, the first transmission device driving a third transmission device, whereas the third transmission device driving an eccentric cam, wherein an eccentric spindle is connected to a lever weight to pull the massage head support to perform tapping, thereby allowing the two massage heads to perform tapping-based massage.

2 Claims, 6 Drawing Sheets

MASSAGE APPLIANCE CAPABLE OF SYNCHRONOUS KNEADING AND TAPPING

BACKGROUND OF THE INVENTION

1. Technical Field

The present invention relates to massage appliances, and more particularly, to a massage appliance which is capable of synchronous kneading and tapping and comprises a power-driven vertically-moving device for driving two kneading devices and two tapping devices to move vertically so as for the two kneading devices to perform mobile kneading-based massage and for the two tapping devices to perform mobile tapping-based massage.

2. Description of Related Art

People nowadays lead a stressful busy lifestyle and can only find peace of mind at home. However, just because you take a good rest at home, it doesn't mean that the back pain inflicting you due to busy lifestyle and work stress is likely to be relieved. In view of this, the related industrial sector developed conventional massage appliances whereby a user massages the body at home to freshen up and relieve back pain.

The conventional massage appliances operate by simply rubbing or kneading parts of the human body and thus cannot refresh the human body efficiently. Furthermore, the conventional massage appliances perform rubbing or kneading monotonously and invariably and thus offer few choices to consumers; as a result, the conventional massage appliances fail to build customer loyalty. Accordingly, the prior art has room for improvement.

SUMMARY OF THE INVENTION

It is an objective of the present invention to provide a massage appliance capable of synchronous kneading and tapping, comprising: a power-driven vertically-moving device for driving two kneading devices and two tapping devices on a housing portion to move vertically; the two kneading devices for performing mobile kneading-based massage; and the two tapping devices for performing mobile tapping-based massage.

In order to achieve the above and other objectives, the present invention provides a massage appliance capable of synchronous kneading and tapping, comprising: an outer portion, wherein a sliding channel is formed inside the outer portion, and a power-driven vertically-moving device is disposed alongside the sliding channel; a device capable of synchronous kneading and tapping, comprising a housing portion, wherein a power source is disposed inside the housing portion, the power source being a first motor, the first motor driving a first transmission device to rotate, the first transmission device driving a second transmission device to rotate, the second transmission device driving a rotational inclined surface structure to rotate, the rotational inclined surface structure driving an oscillating arm to undergo lateral oscillation, the oscillating arm being coupled to a massage head support, two infrared lamp plates, and two massage heads, such that the two massage heads perform kneading-based massage, whereas the first transmission device drives a third transmission device operate, and the third transmission device drives an eccentric cam to operate, such that an eccentric spindle is connected to a lever weight to thereby pull the massage head support and perform tapping, thereby allowing the two massage heads to perform tapping-based massage.

DETAILED DESCRIPTION OF THE EMBODIMENTS OF THE INVENTION

Figure 1:
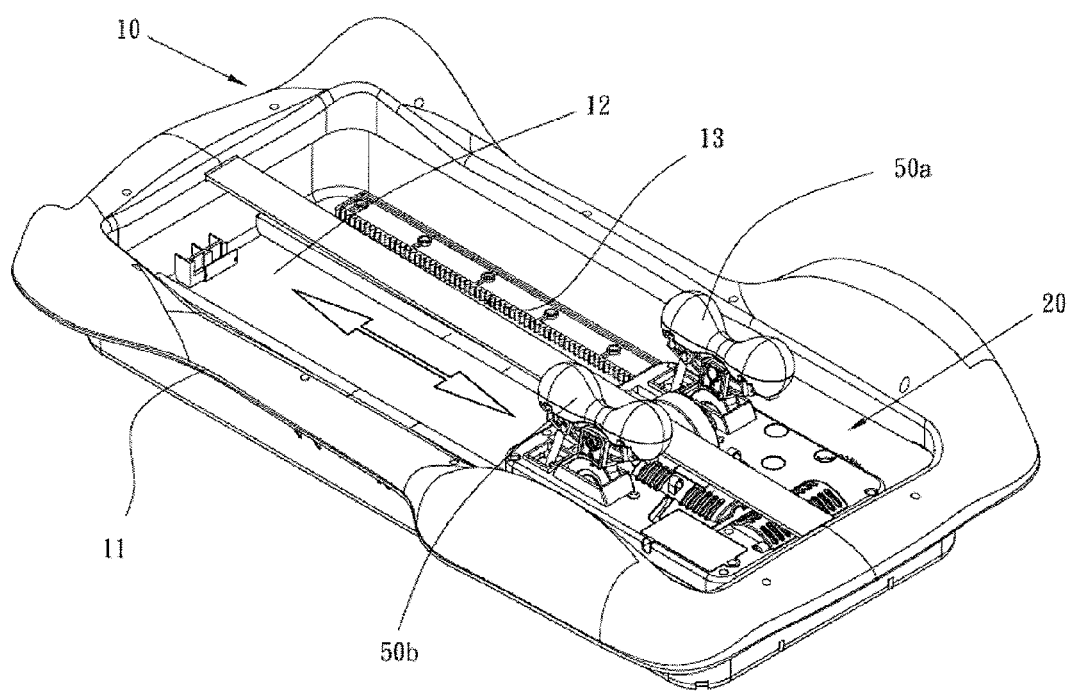
FIG. 1 is a perspective view of a massage appliance capable of synchronous kneading and tapping according to a preferred embodiment of the present invention.
Figure 2:
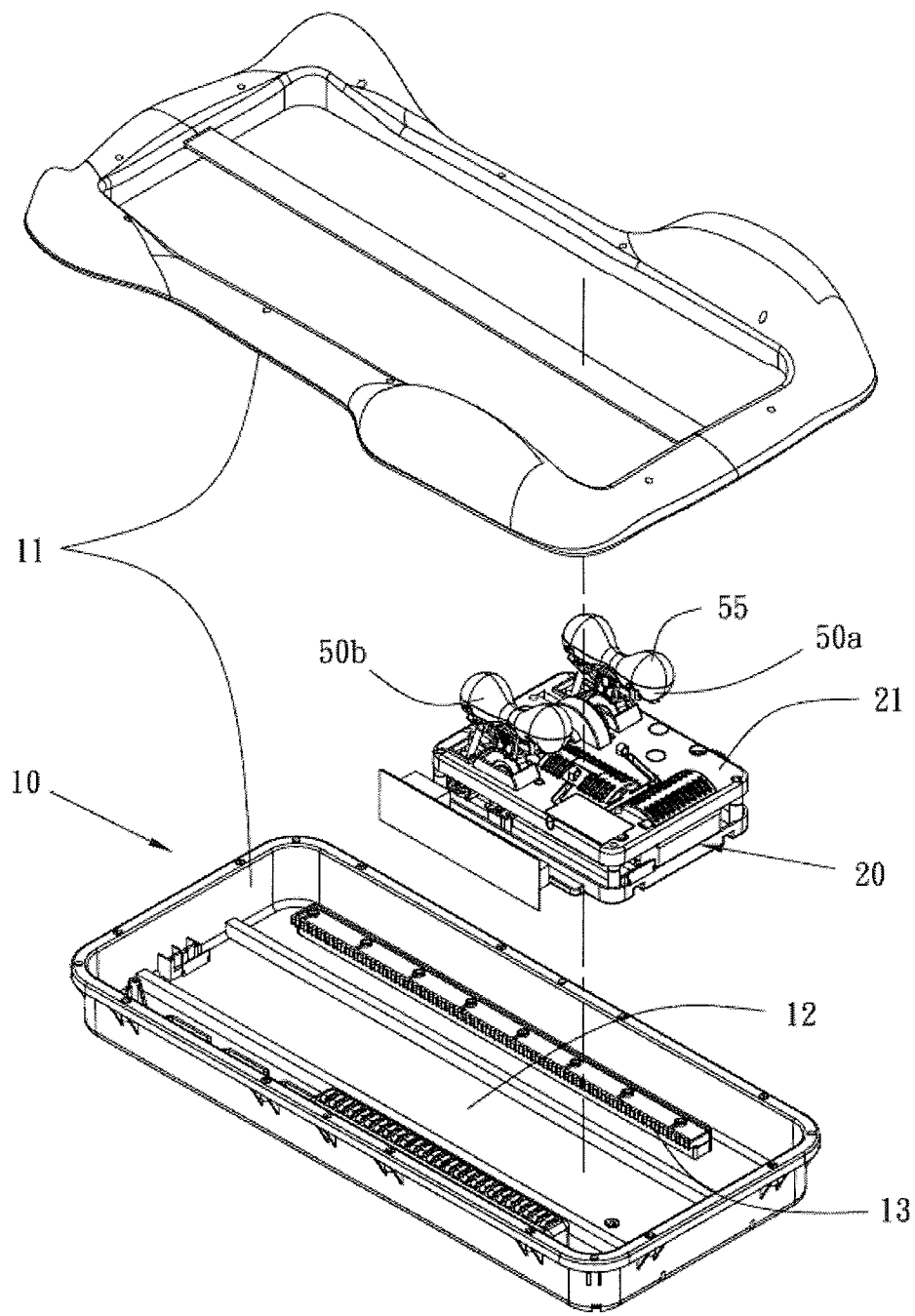
FIG. 2 is an exploded view of the massage appliance capable of synchronous kneading and tapping according to a preferred embodiment of the present invention.
Figure 3:
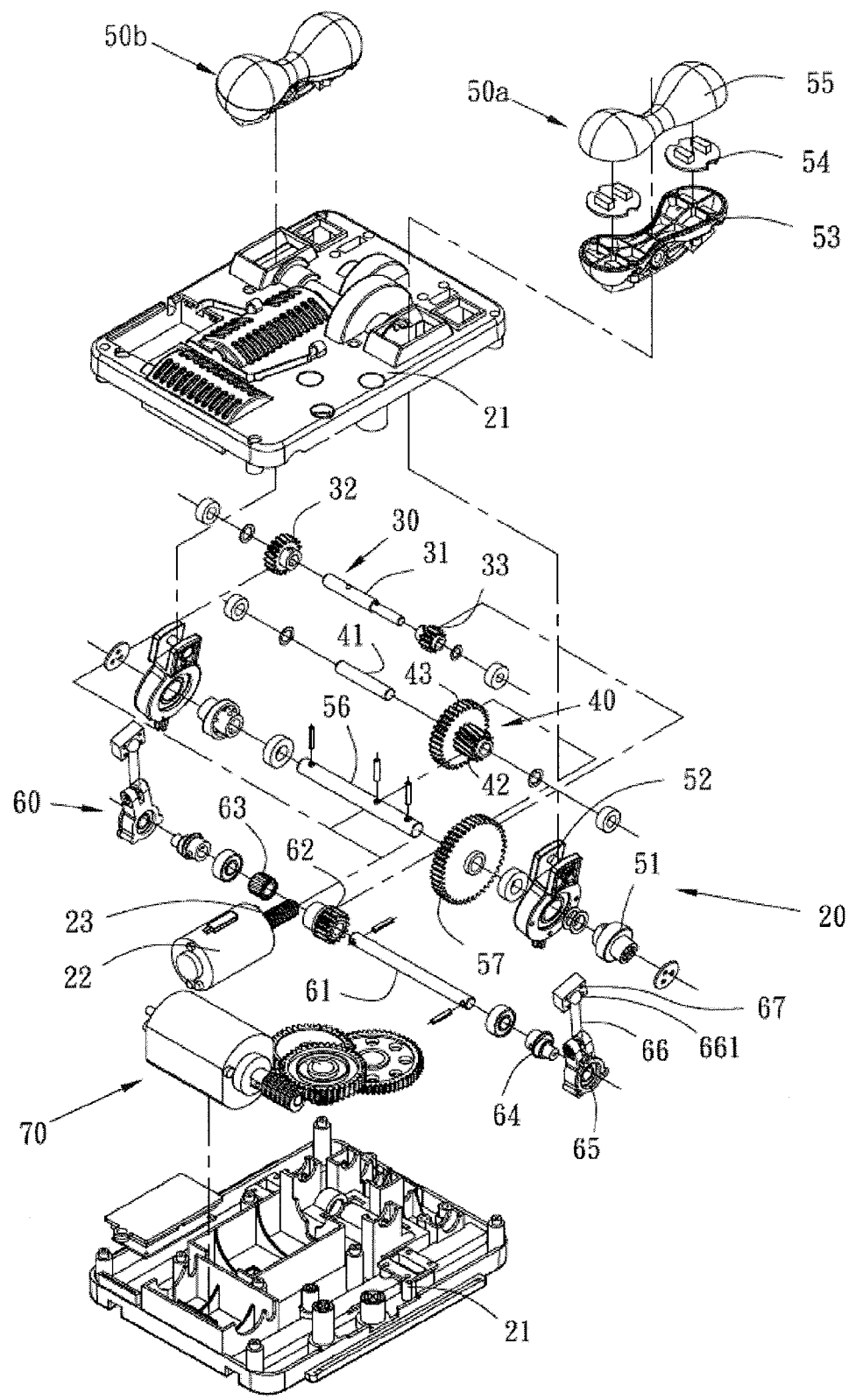
FIG. 3 is an exploded view of a device capable of synchronous kneading and tapping according to a preferred embodiment of the present invention.
Figure 4:
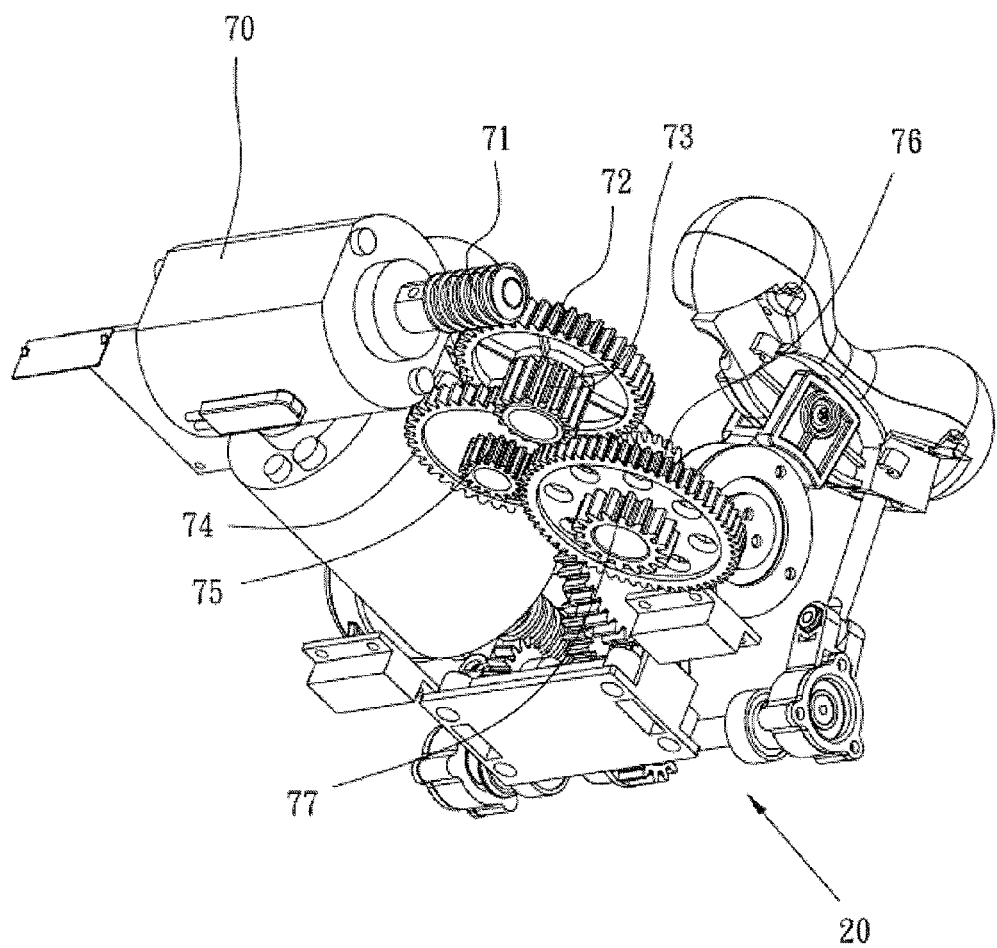
FIG. 4 is a perspective view of the device viewed from the bottom thereof according to a preferred embodiment of the present invention.
Figure 5:
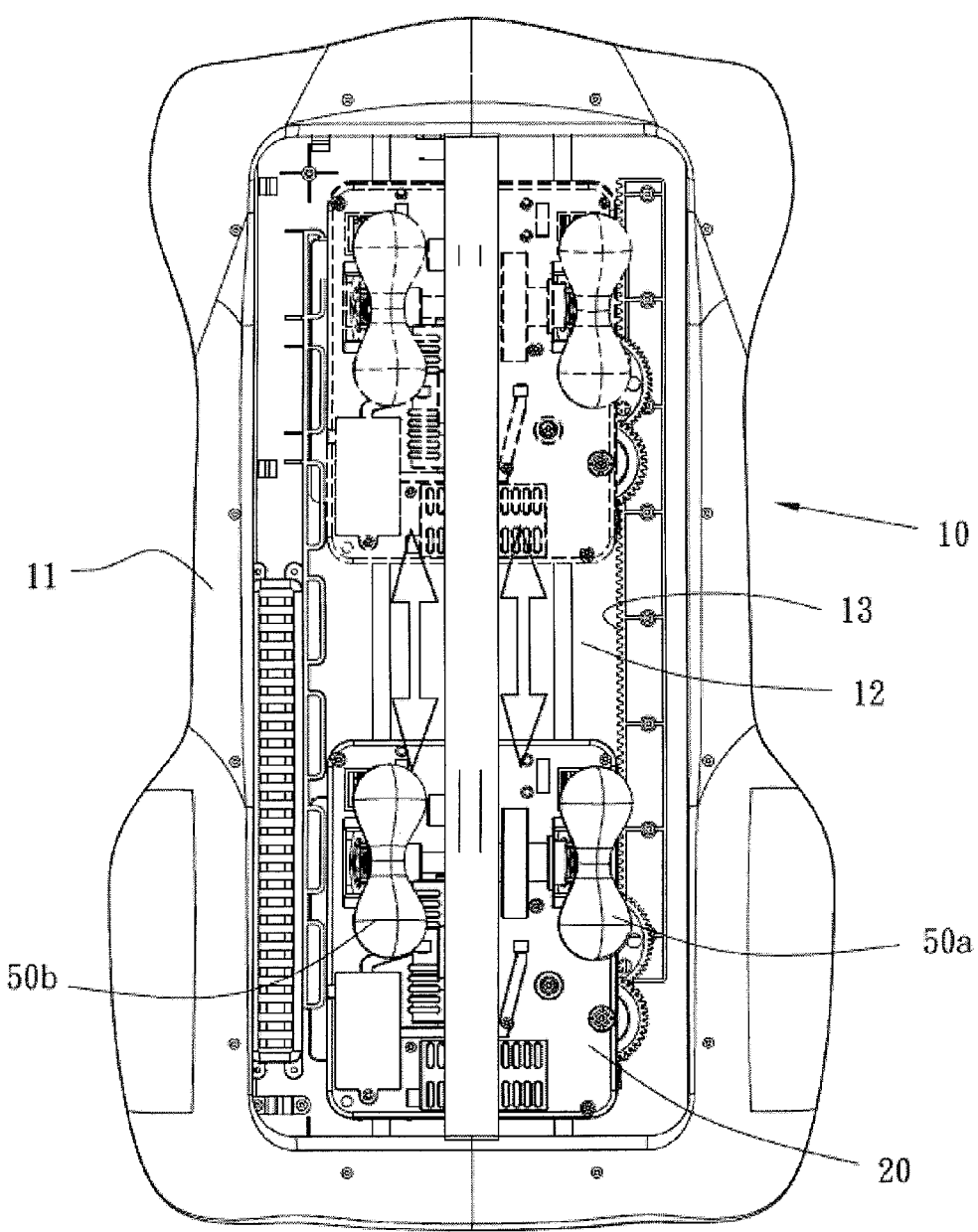
FIG. 5 is a schematic view of ascending/descending massage viewed from the front according to a preferred embodiment of the present invention.
Figure 6:
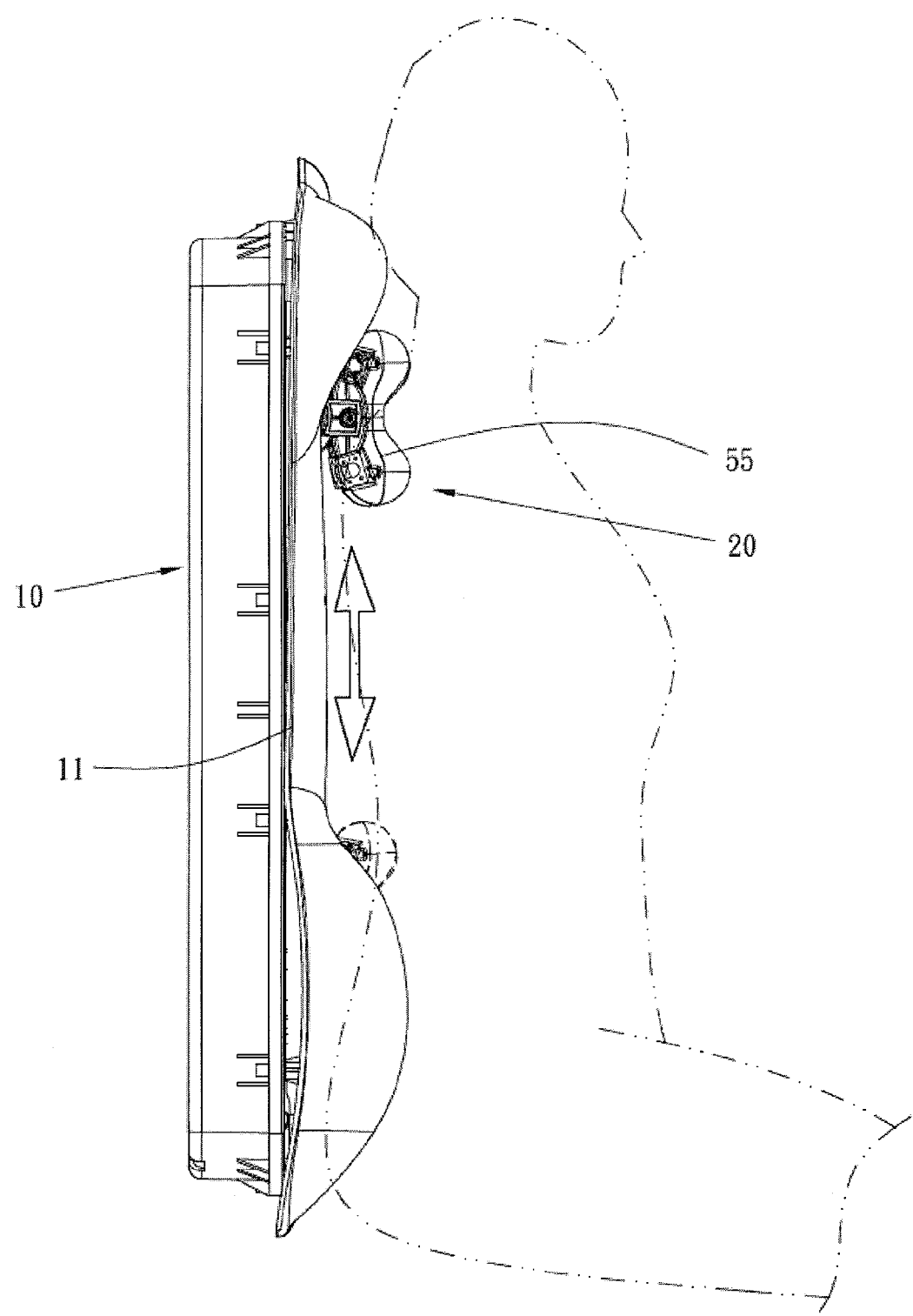
FIG. 6 is a schematic view of ascending/descending massage viewed sideward according to a preferred embodiment of the present invention.

Referring to FIG. 1 through FIG. 6, the present invention provides a massage appliance capable of synchronous kneading and tapping. The massage appliance capable of synchronous kneading and tapping comprises a power-driven vertically-moving device 10, a device capable of synchronous kneading and tapping 20, a first transmission device 30, a second transmission device 40, two kneading devices 50a, 50b, and two tapping devices 60.

The power-driven vertically-moving device 10 comprises an outer portion 11. A sliding channel 12 is formed inside the outer portion 11. A vertically-moving rack 13 is disposed alongside the sliding channel 12.

The device capable of synchronous kneading and tapping 20 comprises a housing portion 21. The device capable of synchronous kneading and tapping 20 further comprises a power source. The power source comes in the form of a first motor 22. The first motor 22 is disposed inside the housing portion 21. A spindle of the first motor 22 is fixed to a worm gear 23.

The first transmission device 30 is disposed inside the housing portion 21. The first transmission device 30 comprises a first transmission shaft 31, a first gear 32, and a second gear 33. The worm gear 23 of the first motor 22 meshes with the first gear 32. The first gear 32 and the second gear 33 which are fixed to the first transmission shaft 31 rotate as a result of the rotation of the worm gear 23 of the first motor 22.

The second transmission device 40 is disposed inside the housing portion 10. The second transmission device 40 comprises a second transmission shaft 41, a third gear 42, and a fourth gear 43. The worm gear 23 of the first motor 22 meshes with the third gear 42. The third gear 42 and the fourth gear 43 which are fixed to the second transmission shaft 41 rotate as a result of the rotation of the worm gear 23 of the first motor 22.

The two kneading devices 50a, 50b extend from the inside of the housing portion 21 to the outside of the housing portion 21. The two kneading devices 50a, 50b each comprise a rotational inclined surface structure 51, an oscillating arm 52, a massage head support 53, two infrared lamp plates 54, and two massage heads 55. The rotational inclined surface structure 51 is fixed to a third transmission shaft 56. A fifth gear 57 is fixed to the third transmission shaft 56. The fifth gear 57 meshes with the second gear 33, such that the first transmission shaft 31 rotates to drive the rotational inclined surface structure 51 to rotate. The oscillating arm 52 abuts against the rotational inclined surface structure 51. The rotational inclined surface structure 51 rotates to drive the oscillating arm 52 to undergo lateral oscillation. The oscillating arm 52 has the massage head support 53 coupled thereto to thereby drive the massage head support 53 to undergo lateral oscillation. The infrared lamp plates 54 and the massage heads 55 are coupled to the massage head support 53. The massage heads 55 are capable of oscillating laterally and thereby performing kneading-based massage on the human body, whereas the infrared lamp plates 54 are effective in applying a heat treatment.

The tapping devices 60 extend from the inside of the housing portion 21 to the outside of the housing portion 21. A sixth gear 62 is coupled to a fourth transmission shaft 61. The sixth gear 62 meshes with the fourth gear 43. A one-way bearing 63 is disposed at the sixth gear 62 and then connected to the fourth transmission shaft 61. Two eccentric cams 64 are disposed at two ends of the fourth transmission shaft 61, respectively. The eccentric cams 64 are each disposed at an eccentric external case 65. Then, the eccentric external case 65 is pivotally coupled to an eccentric spindle 66 with a universal joint 661 connected to a lever weight 67. The lever weight 67 is fixed to the massage head support 53 from beside; hence, as soon as the first motor 22 starts to undergo anticlockwise revolution, the eccentric cams 64 drive the massage heads 55 to perform tapping-based massage. In doing so, the massage heads 55 perform kneading-based massage as well and synchronize kneading-based massage with tapping-based massage.

Therefore, the massage appliance capable of synchronous kneading and tapping is characterized in that: the clockwise rotation of the worm gear 23 of the first motor 22 drives the first gear 32 and the first transmission shaft 31 of the first transmission device 30 to operate, and then the second gear 33 drives the fifth gear 57 and the third transmission shaft 56 to rotate to thereby drive the rotational inclined surface structure 51 to rotate, whereas the rotation of the rotational inclined surface structure 51 causes the oscillating arm 52 to undergo lateral oscillation to thereby drive the massage head support 53 and the two massage heads 55 to undergo lateral oscillation and thus perform kneading-based massage.

Due to the aforesaid components and arrangement thereof, the massage appliance capable of synchronous kneading and tapping is characterized in that: as soon as the worm gear 23 of the first motor 22 starts to rotate anticlockwise, it drives the first gear 32 and the first transmission shaft 31 of the first transmission device 30 to operate, and then the second gear 33 drives the fifth gear 57 and the third transmission shaft 56 to rotate to thereby drive the rotational inclined surface structure 51 to rotate, whereas the rotation of the rotational inclined surface structure 51 causes the oscillating arm 52 to undergo lateral oscillation to thereby drive the massage head support 53 and the two massage heads 55 to undergo lateral oscillation and thus perform kneading-based massage. The anticlockwise torque exerted by the worm gear 23 is transmitted to the third gear 42 and the fourth gear 43. Afterward, with the sixth gear 62, the anticlockwise torque is transmitted via the one-way bearing 63 to the fourth transmission shaft 64 to cause the rotation thereof. Finally, the fourth transmission shaft 64 drives the eccentric cams 64 and the eccentric external case 65 to rotate, whereas the eccentric external case 65 pushes and pulls the eccentric spindle 66 so as to move the lever weight 67 and the massage head support 53, thereby causing the two massage heads 55 to perform kneading-based massage and tapping-based massage simultaneously.

According to the present invention, the housing portion 21 has therein a second motor 70. A spindle of the second motor 70 is fixed to a worm gear 71. A first large gear 72 and a first small gear 73 are integrally formed as a unitary structure. The first large gear 72 meshes with the worm gear 71. A second large gear 74 and a second small gear 75 are integrally formed as a unitary structure. The second large gear 74 meshes with the first small gear 73. A third large gear 76 and a third small gear 77 are integrally formed as a unitary structure. The third large gear 76 meshes with the second small gear 75. The third small gear 77 meshes with the vertically-moving rack 13. The rotation speed decreases according to the gear ratio. The torque increases according to the gear ratio. Hence, it is feasible for the device capable of synchronous kneading and tapping 20 to switch between upward kneading-based tapping-based massage and downward kneading-based tapping-based massage, by switching the second motor 70 between clock revolution and anticlockwise revolution.

What is claimed is:

1. A massage appliance capable of synchronous kneading and tapping, comprising:
  a power-driven vertically-moving device comprising an outer portion, wherein a sliding channel is formed inside the outer portion, and a vertically-moving rack is disposed alongside the sliding channel;
  a device capable of synchronous kneading and tapping comprising a housing portion and further comprising a power source being a first motor disposed inside the housing portion, wherein a spindle of the first motor is fixed to a worm gear;
  a first transmission device disposed inside the housing portion and comprising a first transmission shaft, a first gear, and a second gear, the worm gear meshing with the first gear and rotating to bring about rotation of the first gear and the second gear which are fixed to the first transmission shaft;
  a second transmission device disposed inside the housing portion and comprising a second transmission shaft, a third gear, and a fourth gear, the worm gear meshing with the third gear and rotating to bring about rotation of the third gear and the fourth gear which are fixed to the second transmission shaft;
  two kneading devices extending from inside the housing portion to outside the housing portion and each comprising a rotational inclined surface structure, an oscillating arm, a massage head support, and a massage head, the rotational inclined surface structure being fixed to a third transmission shaft, the third transmission shaft being fixed to a fifth gear, the fifth gear meshing with the second gear, to rotate the first transmission shaft and thereby drive the rotational inclined surface structure to rotate, the oscillating arm abutting against the rotational inclined surface structure, the rotational inclined surface structure rotating to drive the oscillating arm to undergo lateral oscillation, the oscillating arm having the massage head support coupled thereto, thereby driving the massage head support to undergo lateral oscillation, the massage head support having the massage head coupled thereto, thereby driving the massage head to oscillate laterally in a manner to perform kneading-based massage on a human body;
  two tapping devices extending from inside the housing portion to outside the housing portion, a fourth transmission shaft having a sixth gear coupled thereto, the sixth gear meshing with the fourth gear, wherein a one-way bearing is disposed at the sixth gear and then connected to the fourth transmission shaft, wherein two eccentric cams are disposed at two ends of the fourth transmission shaft, respectively, the eccentric cams each being disposed at an eccentric external case, the eccentric external case being pivotally coupled to an eccentric spindle with a universal joint connected to a lever weight, the lever weight being fixed to the massage head support from beside such that, as soon as the first motor starts to undergo anticlockwise revolution, the eccentric cams drive the massage head to perform tapping-based massage, thereby allowing the massage head to perform kneading-based massage in synchrony with tapping-based massage; and a second motor having a spindle fixed to a worm gear, a first large gear and a first small gear integrally formed as a unitary structure, the first large gear meshing with the worm gear, a second large gear and a second small gear integrally formed as a unitary structure, the second large gear meshing with the first small gear, a third large gear and a third small gear integrally formed as a unitary structure, the third large gear meshing with the second small gear, the third small gear meshing with the vertically-moving rack, to thereby decrease rotation speed and increase torque according to a gear ratio, such that the device capable of synchronous kneading and tapping switches between upward kneading-based tapping-based massage and downward kneading-based tapping-based massage as soon as the second motor switches between clock revolution and anticlockwise revolution.

2. The massage appliance capable of synchronous kneading and tapping of claim 1, wherein the massage head support has thereon an infrared lamp plate and the massage head, such that the massage head oscillates laterally and thereby performs kneading-based massage on the human body, whereas the infrared lamp plate are effective in applying a heat treatment.

* * * * *